(12) United States Patent
Hickey et al.

(10) Patent No.: US 8,795,995 B2
(45) Date of Patent: Aug. 5, 2014

(54) METHOD FOR INJECTING A FEED GAS STREAM INTO A VERTICALLY EXTENDED COLUMN OF LIQUID

(75) Inventors: Robert Hickey, Okemos, MI (US); Mark Neville, Raynham, MA (US)

(73) Assignee: Coskata, Inc., Warrenville, IL (US)

(*) Notice: Subject to any disclaimer, the term of this patent is extended or adjusted under 35 U.S.C. 154(b) by 650 days.

(21) Appl. No.: 12/826,991

(22) Filed: Jun. 30, 2010

(65) Prior Publication Data

US 2012/0003707 A1 Jan. 5, 2012

(51) Int. Cl.
| | | |
|---|---|---|
| *C12P 7/06* | (2006.01) | |
| *C12P 7/16* | (2006.01) | |
| *C12P 7/04* | (2006.01) | |
| *C12P 7/02* | (2006.01) | |
| *C12P 7/00* | (2006.01) | |
| *C12M 1/00* | (2006.01) | |

(52) U.S. Cl.
CPC ............... *C12P 7/065* (2013.01); *C12M 29/06* (2013.01); *Y02E 50/17* (2013.01)
USPC ........... 435/161; 435/160; 435/157; 435/155; 435/132

(58) Field of Classification Search
USPC ....................................... 435/161
See application file for complete search history.

(56) References Cited

U.S. PATENT DOCUMENTS

| | | |
|---|---|---|
| 4,162,970 A | 7/1979 | Zlokarnik |
| 4,426,450 A | 1/1984 | Donofrio |
| 4,683,122 A | 7/1987 | Concordia et al. |
| 5,173,429 A | 12/1992 | Gaddy et al. |
| 5,593,886 A | 1/1997 | Gaddy |
| 6,136,577 A * | 10/2000 | Gaddy .......................... 435/161 |
| 6,872,867 B1 | 3/2005 | Senetar |
| 7,285,402 B2 | 10/2007 | Gaddy et al. |
| 2008/0176301 A1 | 7/2008 | Granda et al. |
| 2008/0257812 A1 | 10/2008 | Cardoso Marques Ferreira |
| 2008/0299650 A1 | 12/2008 | Krieg |
| 2009/0035848 A1 | 2/2009 | Hickey |

FOREIGN PATENT DOCUMENTS

WO 0208438 A2 1/2002

OTHER PUBLICATIONS

Henstra et al., Current Opinion in Biotechnology, 2007, 18, 200-206.*
Worden et al., Mass-Transfer Properties of Microbubbles. 2. Analysis Using a Dynamic Model, 1998 American Chemical Society and American Institute of Chemical Engineers, Published on Web Jan. 14, 1998, Biotechnol. Prog. 1998. 74. 39-46.

(Continued)

*Primary Examiner* — Sharmila G. Landau
*Assistant Examiner* — Sheridan MaCauley (57) ABSTRACT

A process for conversion of syngas to liquid products that serve as surface acting agents uses the gas stream at a relatively low pressure to eliminate the use of a compressor. The process uses a liquid stream as the primary energy input to a gas injector that intensely mixes gas and the liquid with reduced compression costs while the presence of the liquid product maintains the gas-liquid dispersion as it flows downward to build a static pressure head. The process lowers the required gas pressure by adjusting the elevation of the gas injector such that a conduit receives the gas-liquid dispersion from the outlet of the injector and confines it as it travels downward to enter the bottom of a column of liquid. The liquid product provides a surface acting agent that prolongs the creation and duration of microbubbles in the gas-liquid dispersion.

21 Claims, 8 Drawing Sheets

(56) References Cited

OTHER PUBLICATIONS

Bloor et al., High Rate Aerobic Treatment of Brewery Wastewater Using the Jet Loop Reactor, Wat. Res. vol. 29, No. 5, pp. 1217-1223. 1995.

Bredwell et al., Mass-Transfer Properties of Microbubbles. 1. Experimental Studies, 1998 American Chemical Society and American Institute of Chemical Engineers, Published on Web Jan. 14, 1998, Biotechnol. Prog. 1998. 14. 31-38.

Bredwell et al., Reactor Design Issues for Synthesis-Gas Fermentations, 1999 American Chemical Society and American Institute of Chemical Engineers, Published on Web Oct. 1, 1999; Biotechnol. Prog. 1999, 15, 934-844.

Dursun et al., Mass transfer and hydrodynamic characteristics in a co-current downflow contacting column, 2003 Society of Chemical Industry; J Chem Technol Biotechnol 78:446-451 (online; 2003).

Engin et al., Modeling and Parameter Identification of a Jet-loop Bioreactor, Proceedings of the 2007 American Control Conference, Marriott Marquis Hotel at Times Square, New York City, USA, Jul. 11-13, 2007, FrC19.4, 6122-6127.

Fadavi et al., Gas-liquid mass transfer in a novel forced circulation loop reactor, Chemical Engineering Journal 112 (2005) 73-80.

Jamshidi et al., Studies on the hydrodynamic behavior and mass transfer in a down-flow jet loop reactor with a coaxial draft tube, 2001 Society of Chemical Industry; J Chem Technol Biotechnol 76: 39-46 (2001).

Krishna et al., Influence of Alcohol Addition on Gas Hold-Up in Bubble Columns: Development of a Scale Up Model, Int. Comm. Heat Mass Transfer, vol. 27, No. 4, pp. 465-472, 2000.

Kundu, et al., Experimental Studies on a Co-Current Gas-Liquid Downflow Bubble Column, Int. J. Multiphase Flaw, vol. 21, No. 5, pp. 893-906, 1995.

Mandal, et al., Gas-holdup distribution and energy dissipation in an ejector-induced downflow bubble column: the case of non-Newtonian liquid, Chemical Engineering Science 59 (2004) 2705-2713.

van Dierendonck, et al., Loop Venturi Reactor—A Feasible Alternative to Stirred Tank Reactors?, Ind. Eng. Chem. Res., vol. 37. No. 3. 1998, 734-738.

Ferreira, Antonio M.C.M., "Jet-Loop System—a New Energy Efficient and Near Zero Sludge Excess Production for Aerobic Wastewater Treatment Using Atmospheric Oxygen Driven to the Effluent by Ejectors", Valorsabio, 10 pgs., Date Unknown, Metadata Creation Date: Oct. 29, 2005, Metadata Modification Date: Sep. 17, 2010, Archive.org Date: Nov. 7, 2010.

* cited by examiner

METHOD FOR INJECTING A FEED GAS STREAM INTO A VERTICALLY EXTENDED COLUMN OF LIQUID

FIELD OF THE INVENTION

This invention relates to the mixing of a feed gas comprising CO, $CO_2$, and $H_2$ with a liquid medium comprising an aqueous alcohol stream to create a fine dispersion of feed gas in a liquid phase conversion zone comprising a deep fermentation vessel.

DETAILED DESCRIPTION

Background

The conversion of gas stream components by contact with a conversion medium in a liquid phase is well practiced in many fields. Where the solubility of the gas stream is limited, contacting and conversion of the gas stream components requires that the gas stream be well disbursed within the liquid medium as a fine dispersion to increase the mass transfer between the gas phase and the conversion media in the liquid phase. This dispersion of gas into liquid streams is energy intensive and typically requires compression of the gas stream to provide the necessary energy to create a high dispersion of gas in liquid phase contacting mediums.

A wide variety of devices are known for the dispersion of gas into a liquid medium. Such devices include venturi injectors, slot injectors or jet injectors and other high pressure mixers. Such gas transfer devices have found widespread use in a variety of fields including those of wastewater treatment and fermentation.

It is an object in these gas liquid contactors to obtain a high rate of reaction of the chemical or biological materials undergoing conversion. Obtaining a high rate of reaction often requires overcoming mass transfer limitations. To this end, the mixing of the liquid and gas is designed to create a high interfacial area between the two phases to maximize gas absorption/transfer as the gas components get dissolved and subsequently converted in the liquid phase. Reducing the size of the gas bubbles in the liquid increases the interfacial area and aids in overcoming mass transfer limitations for the reaction or biological conversion.

Most desirably the liquid will entrain the gas as a fine dispersion of microbubbles. Creating the dispersion of microbubbles requires high energy input. Once created, the microbubbles will begin coalescing into larger bubbles and gas slugs. Therefore, typical practice minimizes the transport of the gas dispersion from the point of its creation to its point of contact with the conversion media.

U.S. Pat. No. 4,683,122 shows the use of multiple jet nozzles positioned in the head space of a gas-liquid reactor for discharging a gas-liquid mixture into a lower portion of the reactor vessel. The primary input for reaction gas in the '122 reference requires compression of the gas supply.

Dispersing gas into liquid media is of particular interest in the field of fermentation due to the increased emphasis on the conversion of renewable energy sources into liquid products. For example conversion of biomass for biofuel production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology.

One technology path for the production of such biofuels is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, propanol, n-butanol or chemicals such as acetic acid, propionic acid, butyric acid and the like. This path can be very efficient since the gasification step can convert all of the components to syngas with good efficiency (e.g., more than 75% of the energy can be available as fermentable compounds), and some strains of anaerobic microorganisms can convert syngas to ethanol, propanol, n-butanol or other chemicals with high (e.g., greater than 90% of theoretical) efficiency.

However, this technology path requires that the syngas components CO and $H_2$ be efficiently and economically dispersed or dissolved in the aqueous medium and transferred to anaerobic microorganisms that convert them to the desired products. And very large quantities of these gases are required. For example, the theoretical equations for CO or $H_2$ and $CO_2$ to ethanol are:

$$6\ CO + 3\ H_2O \rightarrow C_2H_5OH + 4\ CO_2$$

$$6\ H_2 + 2\ CO_2 \rightarrow C_2H_5OH + 3\ H_2O$$

Thus 6 moles of relatively insoluble gases such as CO or $H_2$ have to transfer to an aqueous medium for each mole of ethanol produced. Other products such as acetic acid and n-butanol have similar large stochiometric requirements for these gases.

Many devices and equipment are used for gas transfer to microorganisms in fermentation and waste treatment applications. Most of these reactors or systems are configured for use with microorganisms in planktonic or suspended form i.e. they exist as individual cells in liquid medium. Such reactors or bioreactors contain a large volume of liquid and typically have a liquid height of 10 meters or more to retain enough suspended microorganisms for contact with the gas and to achieve the desired conversion.

These numerous reactors or bioreactors all suffer from various drawbacks in achieving the degree of mass transfer desired for optimum efficiency and productivity (mass of ethanol produced per unit volume-time). In these conventional bioreactors and systems, agitators with specialized blades or injection nozzle configurations are often used. In some configurations such as gas lift or fluidized beds, liquids or gases are circulated via contacting devices.

In some conventional fermentation reactors gas dissolution is accomplished using gas sparging systems or sparging systems operated in concert with impeller-type mixers. These systems, to meet the dual objectives of high gas transfer rate and high gas transfer efficiency (utilization of the fermentable components $H_2$ and CO in the syngas feed), need to economically use syngas in fermentation systems that comprise either deep tanks or pressurized vessels. In either case there is the need to compress (pressurize) the syngas to at least several atmospheres gauge. The use of large compressors complicates the operation of such system which in turn adds to both the capital and operating expense of such operations.

In the field of fermentation, the use of gas injection devices is known to disperse gas streams into liquids. U.S. Pat. No. 4,426,450 discloses a fermentation vessel that uses a plurality of jet injectors to mix air and a fermentation broth in the bottom of a fermentation vessel. To maximize the duration of the gas bubbles in the liquid medium the dispersion gets released near the bottom of the fermentation vessel. Thus, the '450 reference requires a gas stream at sufficient pressure to overcome the hydraulic pressure of the liquid near the bottom of the vessel.

Making biological production of alcohols or other liquid products from syngas commercially feasible requires the retention of large volumes of fermentation liquid. For example a single commercial scale fermentation vessel may need to hold on the order of 4,000 cubic meters or more of fermentation liquid. These vessels will typically have a liquid depth of 15 to 20 meters or more. At such depths the hydrostatic pressure will exceed 150 to 200 kPa and would necessitate compression of the syngas stream to inject it as a feed to the lower portion of a deep fermentation vessel.

Compressing a syngas stream poses special problems. Derivation of the syngas from biological sources may leave residual materials in the syngas that challenge the operation of compressors. For example, the syngas may contain residual fine particulate material. Depending on the gasification operation that syngas may also contain high molecular weight hydrocarbons such as tars. Either of these materials can damage compressors that may be needed to create the necessary gas pressure to create high gas dispersion.

As a result commercial scale operations for the production of liquid products from syngas would benefit from process arrangements that can deliver feed gas to the bottom of deep vessels without the need for large compressors. Therefore, processes are sought that can eliminate the need for large compressors to deliver feed gas to the bottom of deep fermentation tanks.

SUMMARY OF THE INVENTION

This invention is a process for the commercial scale production of liquid products in a deep fermentation vessel by injection of a feed gas stream into a lower portion of the vessel without the need for a compressor. It has now been discovered that the fermentation liquid, when it contains alcohol or other surface tension reducing chemical as a liquid product, can serve as a motive liquid to provide the primary energy input for highly dispersing the feed gas into the fermentation liquid phase as a gas-liquid dispersion at an elevated location and that the dispersion remains stable throughout its transport to lower locations of the fermentation vessel. An appropriate downward velocity in the transporting conduit is needed to maintain a stable dispersion. In this manner the feed gas stream passes at low pressure into contact with a circulating stream of the fermentation liquid. Mixing of the gas and the liquid takes place at a relatively high elevation with respect to the level of the liquid in the vessel so that the required feed gas pressure remains below the level that would require a compressor.

This invention recognizes the commercial advantages of reducing any needed compression of the gas stream to the point where an ordinary blower can supply enough pressure for dispersing the feed gas into the liquid medium. By injecting a gas stream at lower pressure into a mixing device and using the liquid stream as the primary energy input to the gas injector, this invention achieves the intensity of mixing and supplies the shear forces necessary to cause good mixing and dispersion of the gas stream within the liquid to create a dispersion stream of small microbubbles within the liquid. Thus, this invention accomplishes the elimination of compressors by adjusting the elevations of the gas mixing device that creates the dispersion stream with respect to the discharge point of the dispersion stream into an extended column of fermentation liquid. As part of the invention the fermentation liquid contains a liquid product with properties for stabilizing the dispersion of the gas in the liquid.

In particular the presence of alcohol in the fermentation liquid in conjunction with the use of gas injector allows the transport of the dispersion stream over a significant vertical distance without significant coalescing of the gas bubbles. Thus, the invention places the gas injector that creates the dispersion of gas and liquid at a relatively high elevation with respect to the elevation of the discharge point where the dispersion stream gets discharged into the liquid volume. Keeping the gas injector relatively higher than the point of discharge for the dispersion stream allows a lowering of the inlet pressure for the gas entering the gas injector.

The hydraulic head of liquid created by the injection of the dispersion stream into the vessel at a lower elevation than the gas injector eliminates the need for additional pressure on the outlet side of the gas injector. The downward transport of the dispersion stream in a confined conduit creates a static pressure head that compresses the dispersion stream before it enters the vessel. Injection of the feed gas into the fermentation liquid does lower the density of the gas-liquid dispersion relative to the fermentation liquid. Raising the outlet pressure of the gas injector can compensate for any loss in static pressure at the discharge point where the dispersion stream enters the fermentation vessel. The pressure of the dispersion stream at the discharge point may also be raised by elevating the gas injector location relative to the liquid level in the fermentation vessel. Elevating the gas injector adds net static pressure to the dispersion stream due to the increased height of the water column thereby increasing the pressure of the dispersion stream at the discharge point.

This raising of the gas injector elevation does not significantly increase the liquid side pressure required in the gas injector. As a result the gas phase still enters the gas injector at a relatively low pressure. The invention thereby eliminates or reduces the need for compression of the gas stream to the point where a compressor is not required. Instead, the pumping of the fermentation liquid as the motive fluid and the downward transport of the dispersion stream provides all of the necessary pressure to inject the gas-liquid dispersion into the fermentation vessel at a relatively low discharge point. In this manner the process effectively uses the height difference between the gas injector location and the discharge point to raise the pressure of the dispersion stream and eliminate the need for a compressor to supply feed gas to the process.

Accordingly in a broad form this invention is a process for converting a feed gas stream, comprising at least one of CO or a mixture of $CO_2$ and $H_2$, by contact with a fermentation liquid to a liquid product that reduces the surface tension of the fermentation liquid. The process comprises retaining an aqueous fermentation liquid containing a liquid product and microorganisms in a vessel that extends vertically to height such that the fermentation liquid creates more than 100 kPa of hydrostatic pressure. The process withdraws fermentation liquid from the vessel at a withdrawal point and pumps the fermentation liquid as a working fluid to a gas injector. At least a portion of the feed gas stream passes into the gas injector at a pressure of not more than 100 kPa gauge. The gas injector mixes the feed gas stream with the working fluid using the pumping of the working fluid as the primary energy input to create a gas-liquid dispersion from the feed gas stream and the working fluid. The process downwardly transports the gas-liquid dispersion from the gas injector in a dispersion conduit for a distance of at least 10 meters below the gas injector and discharges the gas-liquid dispersion from the dispersion conduit into the vesselat a discharge point located at least 10 meters below the gas injector. Contact of the microorganisms with fermentation liquid that contains dissolved feed gas from the gas-liquid dispersion converts at least one of CO or a mixture of $CO_2$ and $H_2$ to the liquid products in the vessel. The process passes a portion of the fermentation liquid from the vessel to a product recovery zone and recovers a product stream comprising the liquid product from the product recovery zone.

In another broad form this invention is a process for converting a feed gas stream, comprising at least one of CO or a mixture of $CO_2$ and $H_2$, to a liquid product by contact with a fermentation liquid wherein the liquid product reduces the surface tension of the fermentation liquid. The process retains an aqueous fermentation liquid comprising a liquid product and microorganisms in a vessel and partially fills the vessel to a height of at least 10 meters. Fermentation liquid is withdrawn from the vessel at a withdrawal point and pumped as a working fluid to a gas injector having an injector with a location in the vertical direction no lower than the proximate location of the withdrawal point. At least a portion of the feed gas stream passes into the gas injector at a pressure of not more than 100 kPa gauge. The feed gas stream mixes with the working fluid in the gas injector using the pumping of the working fluid as the primary energy input to create a gas-liquid dispersion from the feed gas stream and the working fluid. The process downwardly transporting the gas-liquid dispersion from the gas injector in a dispersion conduit having a uniform flow area and discharging the gas-liquid dispersion from the dispersion conduit into the vessel at a discharge point located at least 15 meters below the gas injector. At least one of CO or a mixture of $CO_2$ and $H_2$ gets converted to a liquid product in the vessel by contact of the microorganisms with fermentation liquid that contains dissolved feed gas from the gas-liquid dispersion. A portion of the fermentation liquid passes from the vessel to a product recovery zone that recovers a product stream comprising the liquid product.

The method is enhanced by the presence of the product liquid in the fermentation broth that serves as a surface acting agent that lowers the surface tension to overcome the tendency of the bubbles to coalesce thereby avoiding loss of bubble/liquid interfacial area of the dispersed gas as it travels to a lower elevation of the discharge point. In particular it has been observed that the presence of oxygenates such as ethanol and/or organic acids such as acetic acid in the liquid media at concentrations as low as 0.05 wt % have a profound effect on gas transfer efficiency. In clean water the result of the adding the surface tension agent can provide gas transfer rates greater than 3 times that observed for clean water. Even at 0.05 wt % an increase of more than 50% in the gas transfer rate was observed. The combination of the alcohol as the surface acting agent together with the intense mixing at the elevated gas injector location gives the surprising result of sustaining good dispersion of the gas in liquid as it travels over distances in excess of 20 meters to the discharge point. Preferably the alcohol and/or organic acid is at a total concentration of at least 0.05 wt % and more preferably greater than 0.5 wt %.

The effect of the reduction in surface tension is the generation of smaller bubbles. The more finely divided dispersion of bubbles provides two benefits. The smaller bubbles provide a significantly greater surface area of gas bubbles exposed to the liquid. In addition the greater dispersion of gas compensates for any coalescence of the bubbles that occurs as the liquid-gas dispersion travels downward through the dispersion conduit to the discharge point.

The invention may be used in any arrangement of a bioreactor that retains a volume of a liquid medium for the suspension of conversion medium over an extended vertical distance. This Invention finds particular application to arrangements that suspend microorganisms in vertically extended vessels such as bubble column arrangements or stirred tank reactors. Another form of bioreactor uses a suspended media in a liquid volume and is shown in US Patent Application publication no. 20090035848

This invention is particularly useful for the conversion of gas streams comprising components of syngas in a fermentation liquid. Ordinarily the fermentation liquid will comprise water, microorganisms suspended therein, nutrient chemicals, cell debris from the microorganisms and products produced by the metabolic processes of the microorganisms. The low solubility of the CO and $H_2$ in the primarily aqueous fermentation liquid necessitates a very good dispersion of the gas into the liquid to achieve good mass transfer so that high conversion is efficiently obtained. The inherent presence of various organic compounds from such biological conversions, mostly ethanol, has been found to provide a highly beneficial combination in achieving good gas dispersion with the process arrangement of this invention.

In more specific form this invention is a process for converting a feed gas stream containing CO, $CO_2$ and $H_2$ to ethanol. The process comprises partially filling a vessel with an aqueous fermentation liquid comprising ethanol and microorganisms to a height such that the fermentation liquid creates more than 100 kPa gauge of hydrostatic pressure and off-gas collects above the surface of the fermentation liquid in the vessel. The process withdraws fermentation liquid from said vessel at a withdrawal point located below the surface of the fermentation liquid and pumps the fermentation liquid as a working fluid to a gas injector having a vertical injector location no lower than the withdrawal point. At least a portion of the feed gas stream and off-gas from the vessel passes into the gas injector at a pressure of not more than 100 kPa and preferably not more than 40 kPa greater than the pressure of the fermentation liquid at the withdrawal point. The process mixes the feed gas stream and off-gas stream with the working fluid in the gas injector and uses the pumping of the working fluid as the primary energy input to create a gas-liquid dispersion from the feed gas stream, the off-gas stream and the working fluid. A dispersion conduit downwardly transports the gas-liquid dispersion from the gas injector. The process discharges the gas-liquid dispersion from the dispersion conduit into the vessel at a discharge point located at least 15 meters below the surface of the fermentation liquid. Contact of the microorganisms with fermentation liquid, that contains dissolved feed gas from the gas-liquid dispersion, converts CO and $CO_2$ and $H_2$ to ethanol in said vessel. The process passes a portion of the fermentation liquid from the vessel to an alcohol recovery zone and recovers a product stream comprising alcohol from the product recovery zone.

DETAILED DESCRIPTION OF THE INVENTION

This invention may be used in fermentation processes for the production of liquid products from a gas stream containing at least one of CO or a mixture of $CO_2$ and $H_2$ where the gas stream has a low pressure and the liquid products reduce the surface tension of the fermentation liquid. The invention is particularly applicable to those processes that produce low molecular weight alcohols and corresponding acids such as ethanol, propanol, n-butanol, acetic acid, propionic acid and butyric acid as liquid products in the fermentation liquid. Especially useful process for application of the invention are those that produce ethanol or acetate in a concentration of at least 0.05 wt %.

Many sources of CO, and $CO_2$ and $H_2$ exist. For example, sources of such gases are "waste" gases such as oil refinery waste gases, gases (containing some $H_2$) which are produced by yeast fermentation, gasified cellulosic materials, coal gasification, reformed natural gas etc. Alternatively such gases are not necessarily produced as by products of other processes but may be produced specifically for use in the fermentation reactions within the fermentation vessel. Preferably the preferred source of the CO, $CO_2$ and $H_2$ is syngas and more preferably syngas produced by gasification of readily available low-cost agricultural raw materials. Another source is the reforming of biogas such as can be produced via anaerobic methanogenic treatment of renewable feedstock and wastes (such as the organic fraction of municipal solid waste, high strength industrial wastes, etc.). Another source of CO, and $CO_2$ and $H_2$ for the purposes of this invention is off-gas recovered from the vessel that may also serve as the feed gas stream.

The fermentation liquid will comprise an aqueous suspension of acetogenic microorganisms and various media supplements retained in a fermentation vessel. Suitable microorganisms generally live and grow under anaerobic conditions, meaning that dissolved oxygen is essentially absent from the fermentation liquid. The various media supplements may comprise buffering agents, trace metals, vitamins, salts etc. Adjustments in the media may induce different conditions at different times such as growth and non-growth conditions which will affect the productivity of the microorganisms. US 2008/0057554 A1, the contents of which are hereby incorporated by reference further discloses the conditions and contents of suitable fermentation liquid for bioconversion CO and $H_2/CO_2$ using anaerobic microorganisms.

Bioconversions of CO and $H_2/CO_2$ to acetic acid, n-butanol, butyric acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds,. Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Ser. No 12/272,320 on Mar. 19, 2010. All of these references are incorporated herein in their entirety.

These microorganisms all have the capacity to produce liquid products that will reduce the surface tension of the fermentation liquid in the fermentation vessel. In application of this invention to the conversion CO or a mixture of $CO_2$ and $H_2$ the fermentation vessel will typically comprise a bioreactor that retains the microorganisms suspended in the fermentation liquid. Specific types of bioreactors include bubble column bioreactors and stirred tank bioreactors.

The fermentation vessel can take any form that provides a substantial depth of fermentation liquid. The fermentation vessel will typically rise to a height of at least 10 meters, more typically to height of 15 meters and often to a height of 20 meters or more. The depth of the fermentation liquid will occupy either the full height or nearly the full height of the fermentation vessel. This vessel height will establish a hydrostatic pressure gradient along the vessel. The dispersion of gas and liquid in the dispersion stream must overcome this hydrostatic pressure at the point where it enters the vessel. Thus where the dispersion stream enters at a discharge point of 10 meters below the liquid surface the static pressure head inside the vessel would equal approximately 100 kPa gauge and for a liquid height of 15 meters the static pressure head would equal approximately 150 kPa gauge.

Use of the invention requires a process arrangement that provides a downward flow of the liquid and entrained gas from the outlet of the gas injector in a dispersion conduit that confines the dispersion stream. The dispersion conduit supplies a static pressure head equal to the weight of the dispersion stream over the difference in elevation between the gas injector outlet and the outlet of the confined conduit. The dispersion conduit can have a location completely outside the vessel for retaining the column of liquid or may extend into the vessel so that it is located partially or wholly within the vessel. The dispersion conduit will typically have a uniform flow area over its length to keep the gas-liquid dispersion at a sufficient velocity to prevent bubble coalescence. In other arrangements the dispersion conduit may reside completely inside the vessel in which case the gas injector may also be located completely within the vessel.

The dispersion conduit will charge the dispersion stream into the vessel at its outlet end. The outlet end of the dispersion conduit constitutes the discharge point at which the dispersion stream exits the conduit into the volume of liquid retained within the vessel.

Distributors, nozzles, and other discharge devices may be located at the discharge point of the dispersion stream and comprise part of the dispersion conduit.

Figure 1:
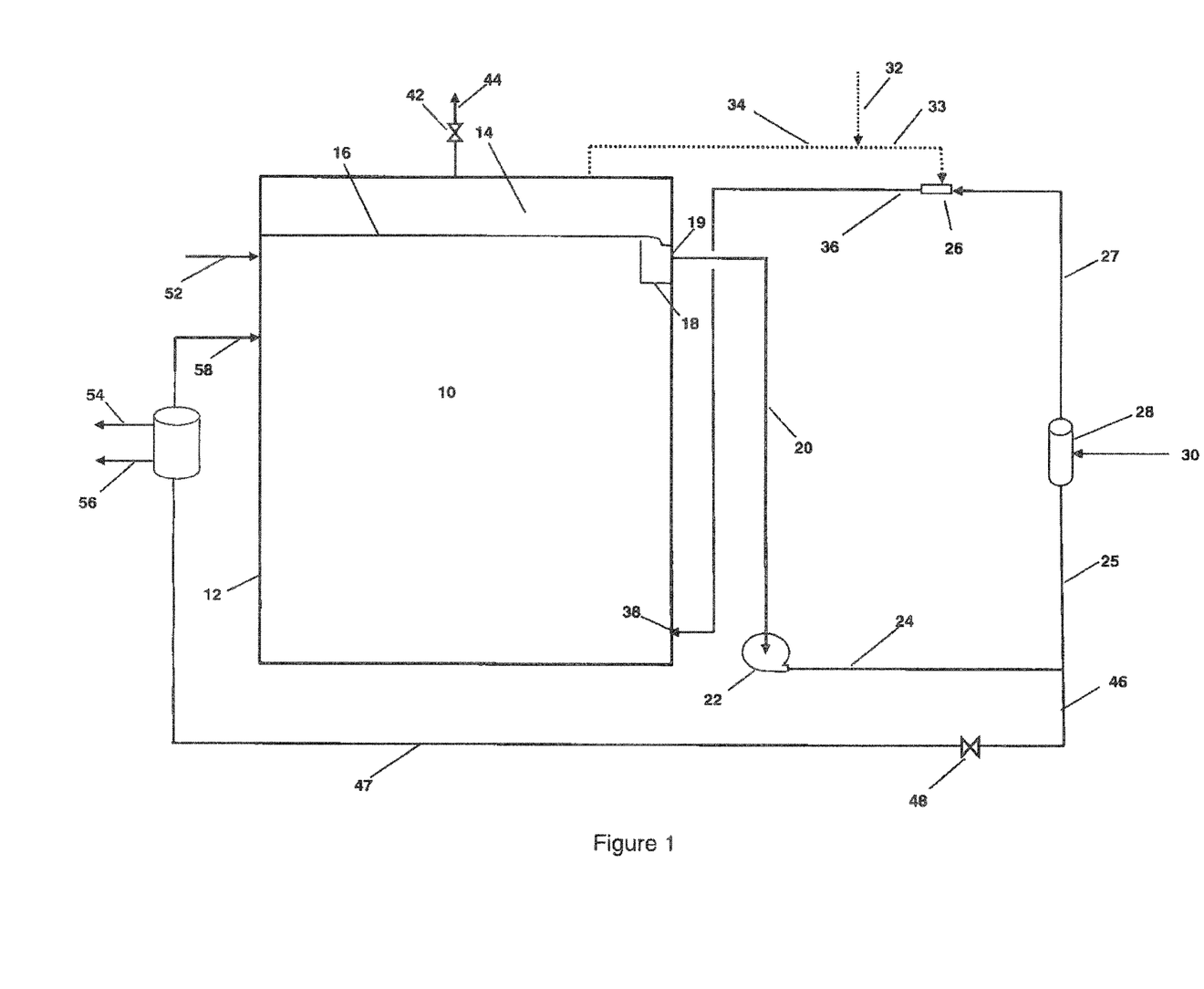
FIG. 1 is a schematic drawing showing a bubble column type reactor with apparatus for practicing the gas injection method of this invention.

A general understanding of the invention and its application is most readily seen in FIG. 1 that shows the vertically extended column of fermentation liquid 10 in a vessel 12. Vessel 12 traps a volume 14 of gas above a liquid surface 16. FIG. 1 schematically shows a process arrangement for the invention that omits equipment that is not essential for an understanding of the invention. A collector 18 provides a location for supply of liquid to a withdrawal point 19 for removing liquid from a location proximate the surface 16 of liquid 10. The collector can provide a means for initially filtering cell material from the fermentation liquid to reduce the amount of microorganisms and organic debris in the liquid withdrawn from the vessel. A conduit 20 carries the liquid from withdrawal point 19 to a pump 22.

Conduits 24, 25 and 27 deliver the withdrawn fluid to a gas injector 26 located at an elevation slightly above the surface 16. An optional mixing chamber 28 can supply additives to the liquid from line 25 A conduit 30 will deliver additives to mixing chamber 28 when provided. A gas stream carried by a conduit 32 flows to gas injector 26 via a conduit 33. Optionally off-gas from gas volume 14 may also flow into injector 26 via a conduit to 34 and conduit 33. A stream of liquid containing a dispersion of gas bubbles leaves injector 26 as a dispersion stream via a conduit 36 and enters vessel 12 at a discharge point 38. A control valve 42 regulates the pressure in entrapped gas volume 14 by the release of off-gas from pressure vessel 10 through a conduit 44. A conduit 52 may provide makeup liquid to the vessel 12.

A conduit 46 withdraws liquid from the vessel 10 via conduit 24 at a rate regulated by a control valve 48 for delivery to a product recovery zone 50 via a conduit 47. Product recovery zone 50 will consist of known equipment arrangements for removal of residual cell material, separation and recovery of liquid products from the fermentation liquid, return of recovered fermentation liquid and purging of waste streams and materials. Suitable equipment arrangement can include filters, distillation columns, membrane systems and other separation equipment. US 2009/0215139 A1 shows an arrangement for a product recovery zone that recovers an ethanol product from a bioreactor. Those skilled in the art can provide suitable equipment to separate the fermentation liquid from conduit 47 into a liquid product stream recovered by conduit 54, a purge stream recovered by conduit 56, and a recycle stream 58 of fermentation liquid having a reduced concentration of liquid product relative to the stream 47.

To achieve maximum benefit from this invention the dispersion stream needs to provide a good distribution of the dispersed gas throughout the liquid in the vessel. Therefore, while the dispersion stream may enter vessel 10 at a single point, the invention functions best when the withdrawal stream enters the vessel at enough points to achieve a good distribution of the gas over the vessel cross section.

Figure 2:
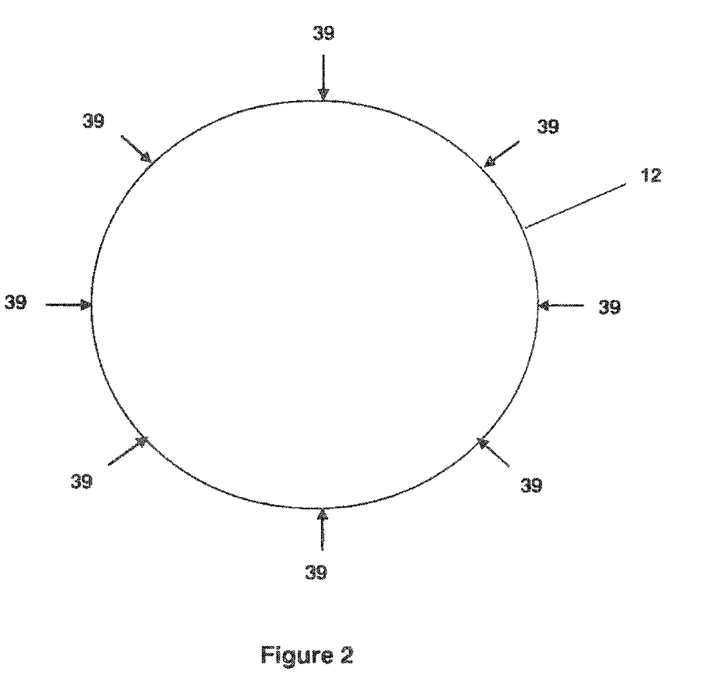
FIG. 2 is a schematic drawing showing the cross section of bioreactor with multiple gas injection points.
Figure 3:
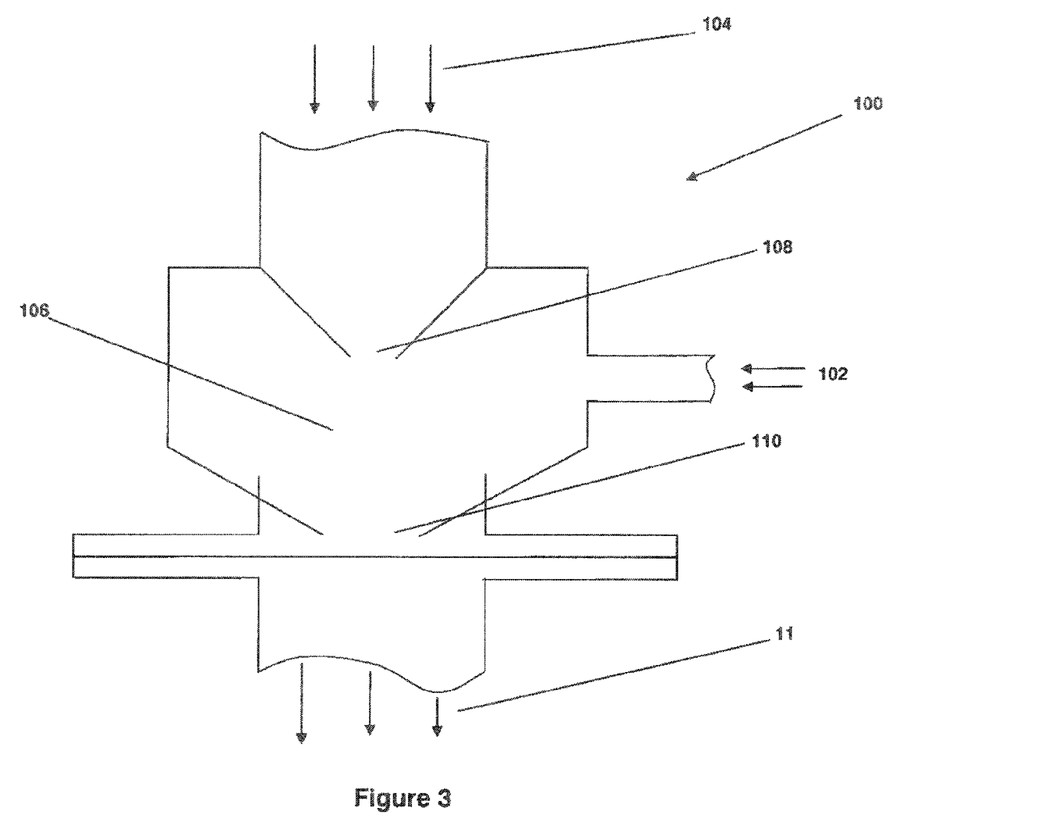
FIG. 3 shows the geometry of a typical gas injection device.

FIG. 2 shows a cross section of the vessel 12 with the multiple discharge points 39 for the dispersion stream spaced evenly about the periphery of the vessel. FIG. 2 shows the injection points external to the vessel 12. This invention may use any method of providing multiple discharge points for the dispersion stream including the use of manifold arrangements within the vessel. In conjunction with the use of multiple discharge points, practice of the invention may include the use of multiple withdrawal points, pumps and injectors to supply the dispersion stream to the various discharge points.

The invention requires the use of a gas injection device that creates the dispersion stream and promotes good mixing of the gas and liquid to disperse the gas as bubbles into the liquid phase. Typical devices include a venturi eductor, a jet injector, or a slot injector. These devices use the liquid flowing through them as the motive liquid and, in accordance with this invention, as the primary means of delivering the energy necessary to create high shear and good dispersion of gas bubbles in the exiting stream. Suitable devices for this invention will use the liquid stream as the primary motive force through the injection device.

Providing the required pressure drop for suitable mixing will comprise one of the main energy inputs into the operation of this process. Pressure drop across these devices will generally range from 100 to 200 kPa. This pressure drop will provide the main energy input for dispersing the gas into microbubbles and in some cases will also serve to induce gas flow into the injection device.

Preferred gas injectors will operate with low requirements for input gas pressure. In most cases the input gas pressure will not exceed 100 kPa and input pressures of 40 kPa or less may be used. Arrangements of the invention as shown herein and as readily appreciated by those skilled in the art can operate with gas pressure at atmospheric or only slightly higher than atmospheric pressure. Operating with some positive gas stream pressure into the gas injector can provide a significant increase in the amount of gas that can be fed to the gas injection device and mixing that is achieved therein while still operating well below the pressure that would require a compressor to deliver gas to the gas injector.

The property of the liquid product in reducing the surface tension of the fermentation liquid significantly increases the volume of gas that can be entrained with the liquid in the gas injector. This enables the gas injector to receive higher volumes of feed gas or recycle gas from the vessel. Thus, the gas entering the gas injector may comprise fresh feed gas, off gas recycled from the vessel or a combination of the feed gas and off gas. Typically the ratio of feed gas or feed gas and off-gas that passes to the liquid entering the gas injector is from 1/1 to 3/1 actual $m^3/m^3$.

Another important operating parameter of the gas injector is the exit velocity of the gas-liquid dispersion at its outlet. This invention uses a difference in elevation between the outlet of the gas injector and the discharge point of the dispersion stream into the column of liquid retained by the vessel to reduce the required discharge pressure on the outlet of the device. Higher exit velocities on the outlet of the gas injector and dispersion conduit minimize the time for bubble coalescence before the dispersion stream gets to the fluid discharge point. Velocity of the dispersion stream downstream of the gas injector is usually in the range of 0.5-2 meters/second. Preferably the dispersion stream will have an average velocity of at least 1 meter/second between the gas injector outlet and the gas discharge point. A particular configuration of this invention will introduce the gas into the gas injector located at a height slightly above the liquid level in the column of liquid and then deliver the resulting fine dispersion of gas/liquid down to the bottom of the column of liquid via a conduit where the downward liquid flow rate is sufficiently high to carry the gas and liquid without coalescence of the micron sized gas bubbles into larger sized bubbles.

Gas entrainment in the dispersion stream lowers its density and reduces the static pressure head of the fluid in the dispersion conduit. A higher elevation of the gas injector relative to the upper surface of the liquid in the vessel raises the static pressure head of the lower density fluid that makes up the dispersion stream. The elevated location of the gas injector relative to the vessel liquid level keeps the outlet pressure of the gas injector relatively low to allow its operation with the low pressure at its gas inlet. Therefore, by varying the elevation of the gas injector, the required inlet pressure of the gas may be adjusted to accommodate a variety of gas injection devices and minimize the gas pressure required.

Venturi devices will allow use of low pressure gas streams or, depending on the elevation of the venturi device, the gas stream may enter the device at atmospheric pressure. A typical arrangement of this invention that uses a venturi device located at an elevation at or above the liquid level in the vessel may receive a gas stream at atmospheric pressure and inject the resulting gas-liquid dispersion through a discharge point located at a liquid depth of 10 meters or more in the vessel. In this manner a process arrangement as shown in FIG. 1, can recycle gas from gas volume 14 with the incoming gas stream from conduit 32 without the need for pressurization of either gas stream.

Jet aerators or slot injectors are another suitable form of gas injection device. Slot injectors are a variant of jet aerators. These devices can operate as venturi devices that draw gas into the device for mixing without supplying a positive gas pressure. These devices may also operate with some positive pressure of the gas stream such that gas at relatively low pressure enters a mixing chamber with a high velocity liquid stream for contact and intense mixing of the liquid under high shear conditions. This results in the formation of micron sized bubbles or microbubbles for injection into the vessel as the dispersion stream. The microbubbles are relatively fine (0.01 to 1.0 mm in diameter and more preferably 0.01 to 0.3 mm in diameter) and their presence aids in dissolving some of the gas into solution with the liquid medium.

FIG. 3 shows the typical internal arrangement of a gas injector 100 in more detail. The injector has an inlet for gas stream 102, an inlet for liquid stream 104, and a mixing zone 106, into which the liquid stream 104 is discharged through an orifice 108. The gas stream 102 meets the liquid stream 104 in the mixing chamber 106 from which a dispersion 112 exits via an outlet orifice 110. Many types of gas injectors are known and commonly used industrially. One model of a preferred type of gas injector is shown in U.S. Pat. No. 4,162,970. Thus the main function of the gas injector is to provide a dispersion stream at the outlet of the gas injector. Any injector that provides a dispersion stream consisting of the gas in the form of highly dispersed bubbles throughout the liquid and that can utilize gas at relatively low pressure will work in this invention.

The dispersion stream may be charged into the liquid column from any direction. Where the dispersion stream enters in a substantially horizontal direction, it may be advantageous for it to enter at a slightly downward angle to increase the inward travel of the dispersion stream across the vessel.

The use of this invention does not require that vessel holding the column of liquid to maintain a separate gas phase above the liquid in the vessel or that the gas injector receive any of the recovered gas from the vessel. Where the vessel containing the liquid maintains a gas phase volume above the liquid volume, the gas injection device may have a relative elevation at, above or below the surface of the liquid. The gas phase, when present, may be at atmospheric pressure or may have a pressure greater than atmospheric pressure to supply gas at slightly elevated pressure to the gas injector. With reference to FIG. 1 the control valve 42 may be used to control pressure maintained in the gas volume 14 and the resulting pressure of the gas flowing to the inlet of injector 26.

Relative to the gas injector, the gas discharge point must have a lower elevation to create downward flow of the dispersion stream from the outlet of the gas injector to its injection point into the liquid column. Arranging for downward flow of the dispersion supplies the difference in elevation necessary to create a hydraulic pressure head between the discharge point 38 and the outlet of gas injector 26. The hydraulic pressure head lowers the overall pressure at the outlet of the gas injector and results in a lower absolute pressure requirement for the gas stream entering the gas injector.

The required difference in elevation from the outlet of the gas injector to the discharge point of the dispersion stream into the vessel will vary depending on the gas injection device, the quantity of gas for injection, the properties of the liquid and other factors particular to the type of contacting required in the column of liquid. The invention usually provides greater benefits as the elevation difference from injector outlet to injection point increases. Typically the difference in elevations equals at least 10 meters and more preferably at least 15 meters. In a preferred arrangement the injector will have a location above the highest liquid level in the fermentation vessel and the hydrostatic pressure in the vessel at the discharge point will be at least 150 kPa gauge.

Liquid for mixing with the gas may be withdrawn from any point in the vessel. In most cases a pump will supply pressure to the withdrawn liquid and impart the needed energy to the motive fluid for the necessary static pressure on the inlet side of the injector. The practice of this invention does not require a particular location of the pump relative to the withdrawal point of the liquid from the vessel. To reduce suction head on the pump preferred arrangements of the invention will locate the pump below the withdrawal point of the liquid. Thus, the pump may be located at some distance below the withdrawal point of the liquid or at any elevation where the column of liquid will provide any amount of hydrostatic pressure desired to reduce the suction head of the pump and to increase the overall discharge pressure of the pump.

Fermentation processes require the addition of chemicals or nutrients to the liquid in the vessel 10. Mixing chamber 28 provides a convenient location for the introduction and mixing of such additives into the vessel via the recirculation of liquid passing through lines 24 and 36.

The method of this invention may supply all of the gas requirements for contact in the liquid column or additional gas may be added by other gas injection means such as bubble aeration systems. Where the dispersion stream enters the liquid column or vessel it will usually do so as a high velocity plume that keeps the bubbles in the highest hydrostatic pressure for a longer time and results in greater gas transfer. The dissipation of the energy in the plume as it expands creates fine eddy currents that help mix any other materials contained in the column of liquid.

A goal of this invention is to reduce gas pressure at the inlet of the gas injector while still supplying a dispersion stream with a highly dispersed gas phase. In addition to keeping a high transport velocity for the dispersion stream, the presence of the liquid product that reduces the surface tension of the fermentation liquid greatly enhances the dispersion of the gas into small gas bubbles and maintains the dispersion in both the dispersion stream and the column of liquid. A resulting increase in the gas transfer rate occurs mainly from the reduced bubble size and increased dispersion of the gas bubbles in the liquid. For example alcohols are known to serve as an effective surface tension altering agent in dispersion of gas into microbubbles within aqueous solutions. In particular the lower surface tension and smaller bubble size resulting from the presence of the alcohol in the resulting fermentation broth can largely overcome any problems of rapid bubble coalescence downstream of the gas injector. The ability of the liquid product to reduce the surface tension avoids the need to add other suitable agents to control surface tension and thereby avoids any deleterious interactions with other substances in the column of liquid that inhibit conversions or contaminate products. Thus this invention works well with processes for the fermentation of gas phase feed especially CO or a mixture of $CO_2$ and $H_2$ and where microorganisms in the column of liquid convert these gas components to alcohol, in particular ethanol.

Figure 4:
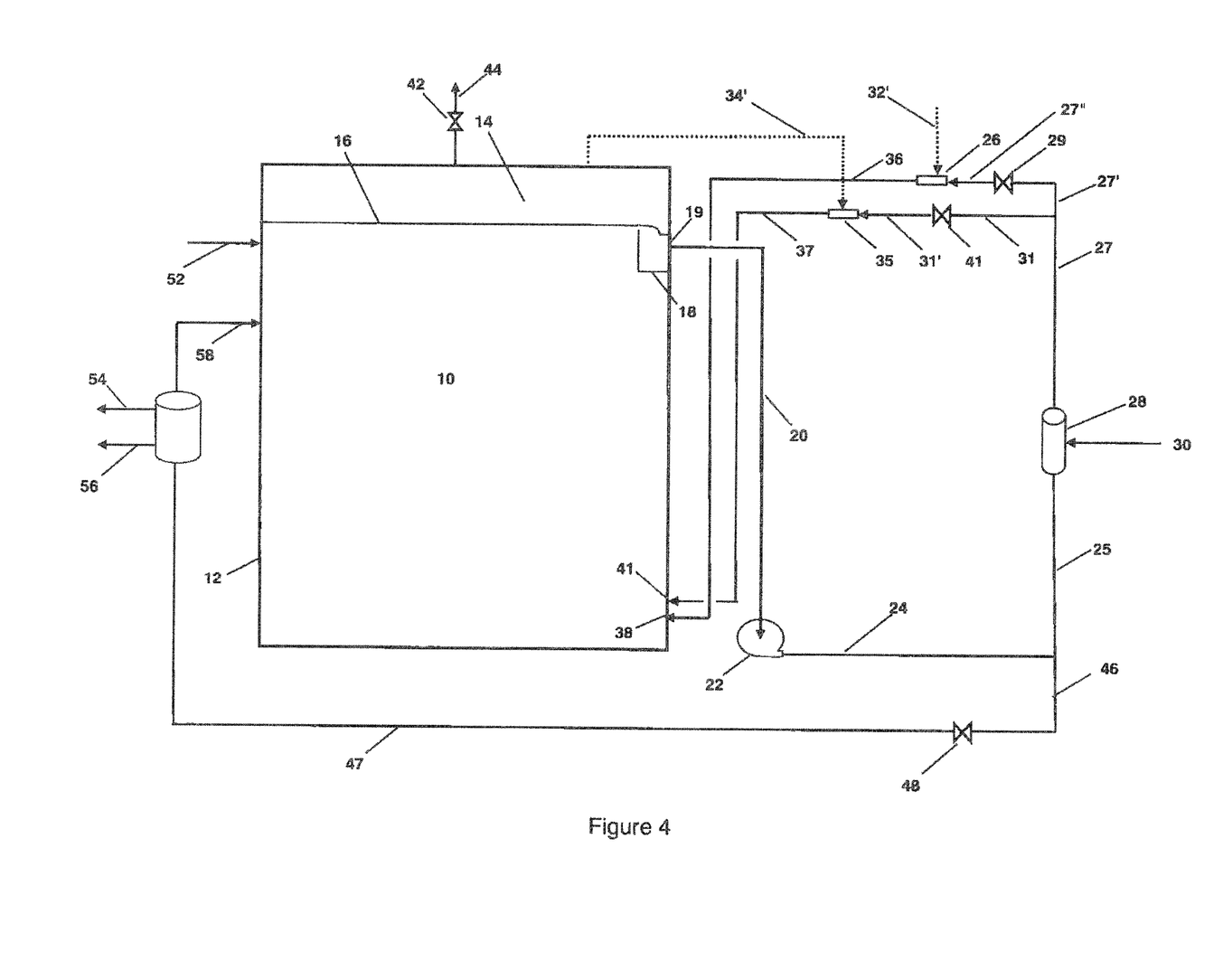
FIG. 4 shows an alternate arrangement for the gas injector of FIG. 1.

In another form the process of this invention uses different gas injectors to disperse the feed gas and the recycle gas into the fermentation liquid. FIG. 4 shows an arrangement where the pumped fermentation liquid from conduit 27 can transfer fermentation liquid to either or both of conduits 27' and 31 as determined by control valves 29 and 41. (All numbered elements of FIG. 4 are the same as FIG. 1 unless otherwise noted.) Any liquid entering conduit 27" will supply fermentation liquid to the gas injector 26 for mixture with feed gas supplied by conduit 32' and the production of a dispersion stream carried to vessel 12 and discharged in the manner previously described. Liquid entering conduit 31' will supply fermentation liquid to a gas injector 35 for mixture with recycle gas supplied by conduit 34' and the production of a dispersion stream carried to vessel 12 by a conduit 37 and discharged through one or more discharge points 41. Thus, in actual practice this invention may only inject feed gas through one set of gas injectors, only inject recycle gas through a different set of gas injectors, or inject both feed gas and recycle through different sets of gas injectors. Many process arrangements may advantageously operate the gas injector for the feed gas at a higher gas inlet pressure and/or gas injector pressure drop as compared to the gas inlet pressure of the recycle gas or pressure drop across the gas injector receiving the recycle gas. In this manner the feed gas that contains the highest concentration of the lesser absorbed gases such as CO and $H_2$ may receive more intense mixing through higher feed gas pressure or greater liquid pressure drop. Conversely the gas injector for the recycle gas may operate with less intensive mixing conditions since it contains higher concentrations of more readily absorbable $CO_2$.

EXAMPLES

Example 1

This example shows the degree of gas dispersion obtained using water with a gas injector located proximate the top of a fermentation vessel that receives a low pressure gas input stream and produces a gas-liquid dispersion that travels downward for approximately 20 meters in a confined conduit for discharge into the bottom of the vessel. This example uses air as the low pressure gas input for health and safety reasons and measures dissolved oxygen in the liquid within the vessel to monitor gas transfer.

Figure 5:
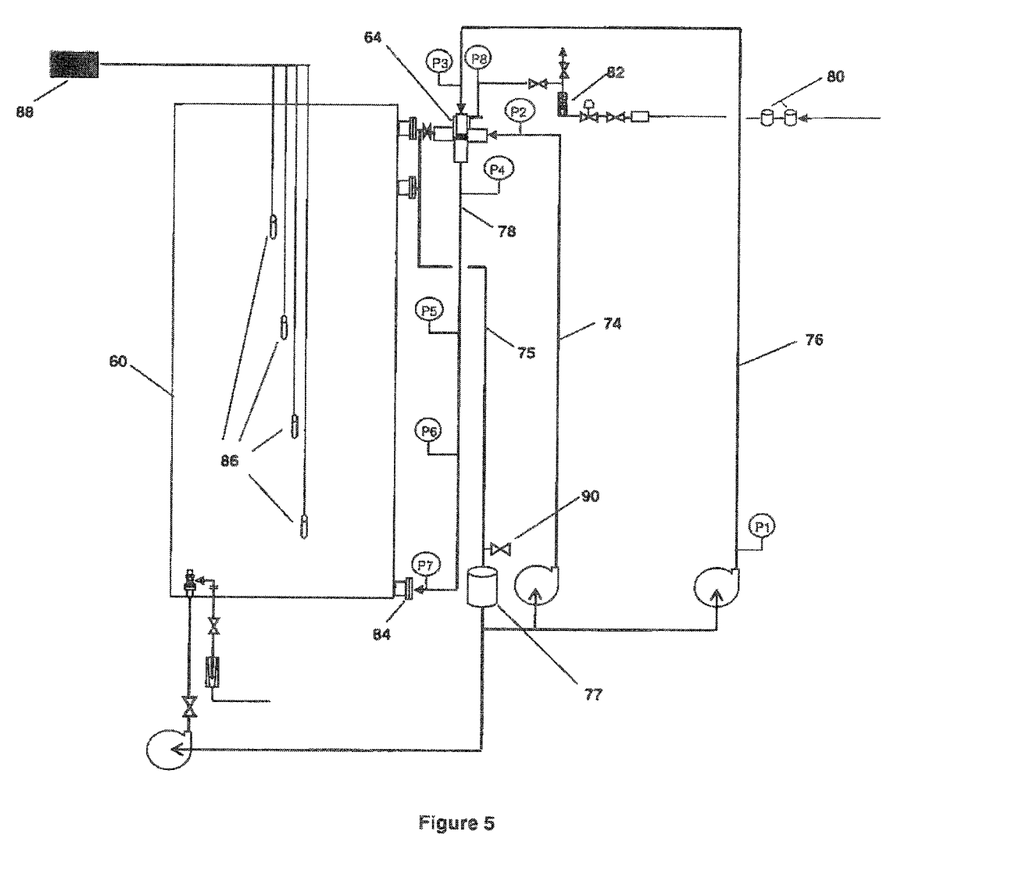
FIG. 5 schematically shows the experimental arrangement for creating and transporting a gas-liquid dispersion.
Figure 6:
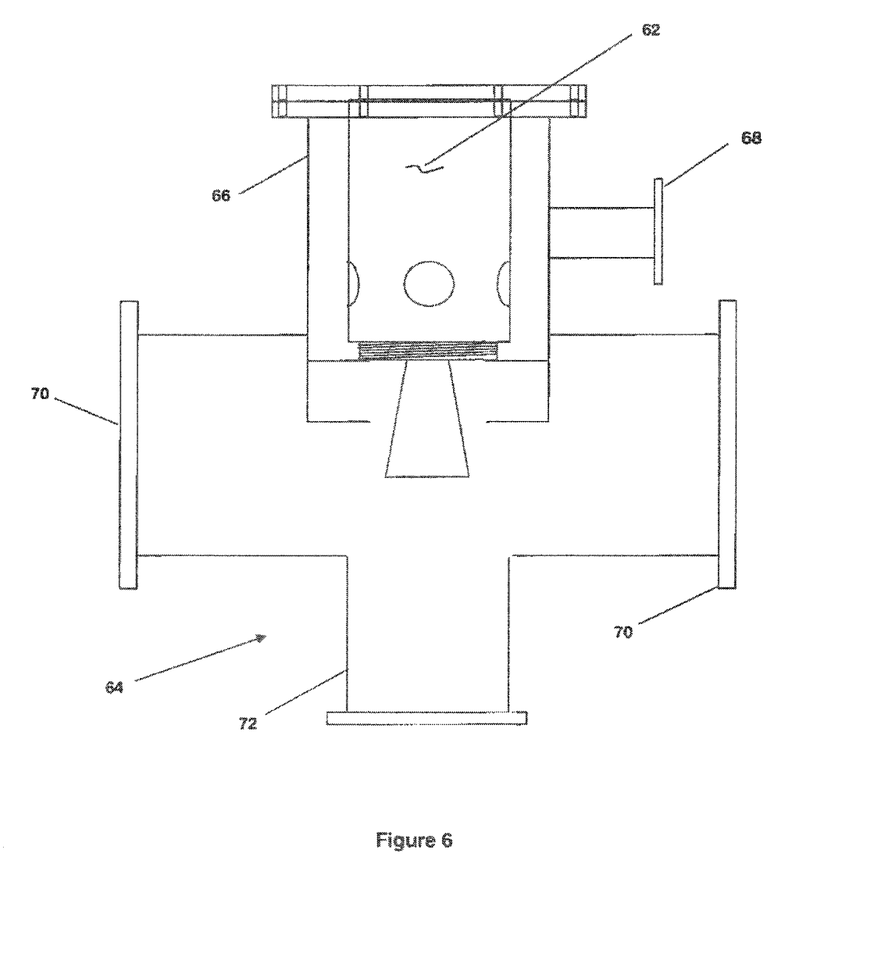
FIG. 6 schematically shows the housing for the gas injector used in the experimental arrangement depicted by FIG. 5.

FIGS. 5 and 6 schematically depict the arrangement of the experimental apparatus for this example. A vessel 60 having a height of 21 meters and a diameter of 1.5 meters retained liquid to height of approximately 19 meters. The gas injector 62 was located at approximately the top of the vessel in a fiberglass reinforced plastic cross 64 having nominal pipe branch sizes of 15 cm×15 cm×15 cm×10 cm. A top pipe branch 66 of the cross having a 15 cm diameter retained the gas injector 62. The gas injector was slot injector model number KSIBJA supplied by $K_L$a Systems Inc. of Assonet, Mass. A 5 cm port 68 in the top pipe branch delivered air to the gas injector. Primary pumped flow entered the top port 66. Secondary pumped flow entered one of the 15 cm side branches 70 for the purpose of increasing the liquid velocity in the downwardly disposed 10 cm pipe branch 72 that delivered the resulting gas-liquid dispersion to the downcomer 78. The risers 74 and 76 that supply liquid for the primary and secondary pumped flow were constructed of 10 cm PVC and the downcomer was constructed using clear 10 cm PVC for physical observation of the gas-liquid dispersion within the confined conduit. A 15 cm conduit 75 supplied the fermentation liquid from vessel and contained a bubble trap 77.

Testing was conducted with the vessel open to the atmosphere using air as the gas and water as the liquid in the vessel. Compressed air was supplied to the gas injector 62. The air stream passed through two coalescing oil filters 80 before passing to the gas injector through a Brooks Model MT 3809 flow meter 82 that quantified the air rate and a globe valve that regulated the gas flow rate. A series of pressure gauges (P1-P8) quantified pressure at the points indicated in FIG. 5. The 10 cm downcomer 78 delivered the gas-liquid dispersion to a 10 cm port 84 located at the bottom of the vessel 60. A line 92 supplied nitrogen for deaeration between experimental runs.

To evaluate the gas transfer efficiency dissolved oxygen was measured on line using four YSI model Pro ODO luminescent optical dissolved oxygen probes (DO probes) 86. The probes were installed at heights of 3 meters, 7.6 meters, 12.2 meters and 16.8 meters from the bottom of the vessel. A guide wire strung through the center of the vessel was used to retain the probes and hold them in the center of the vessel. Data from the DO probes was recorded by data collection terminal 88 at a frequency of every 2 seconds.

Figure 7:
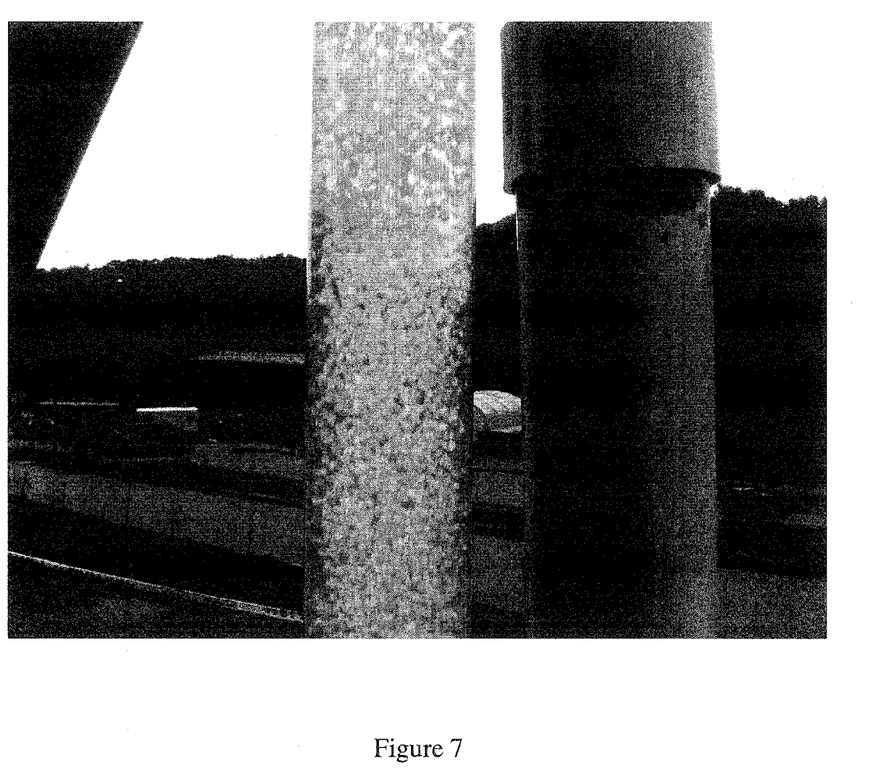
FIG. 7 is a photograph showing a coarse gas-liquid dispersion produced by the experimental apparatus of FIG. 5.

This test was performed using clean water. Conditions during the test period included a total liquid depth of 63 feet in the vessel, a temperature of 21.1° C. and barometric pressure of 742 mm Hg. Samples were taken at a point 90 from line 74. Using a primary liquid flow rate of 370 liters per minute and a secondary liquid flow rate of 450 liters per minute it was found that the maximum gas to liquid ratio at the outlet of the nozzle that could be achieved was 0.69 $Nm^3/m^3$. Above this value significant gas bubble coalescence resulted in slug flow occurring in the downcomer irrespective of the amount of secondary flow that was used. The inlet pressure of the air into the gas injector was 390 kPa. FIG. 7 shows a photo of the best gas mixing achieved with the clean water. The air flow was maintained constant at a value of 260 liters per minute until the dissolved oxygen appeared to reach steady state concentration at the different sampling stations. The ultimate steady-state dissolved oxygen concentrations versus different sampling heights are presented in Table 1. The results indicate that the mixing rate is more rapid than the gas transfer rate and because of this the dissolved oxygen throughout the profile of the entire depth of the vessel are close to the same with the lower depths having dissolved oxygen concentrations less than saturation at that depth and the highest depth have dissolved oxygen concentrations above the calculated saturation concentration.

TABLE 1

| Sampling Depth (Feet from Bottom) | Measured D.O. (mg/L) | Calculated Saturated D.O. (mg/L) | Percent of Saturation |
| --- | --- | --- | --- |
| 10 | 13.9 | 22.2 | 62.6 |
| 25 | 13.9 | 18.3 | 76.0 |
| 40 | 13.8 | 14.5 | 95.2 |
| 55 | 13.2 | 10.7 | 123.4 |

Example 2

Figure 8:
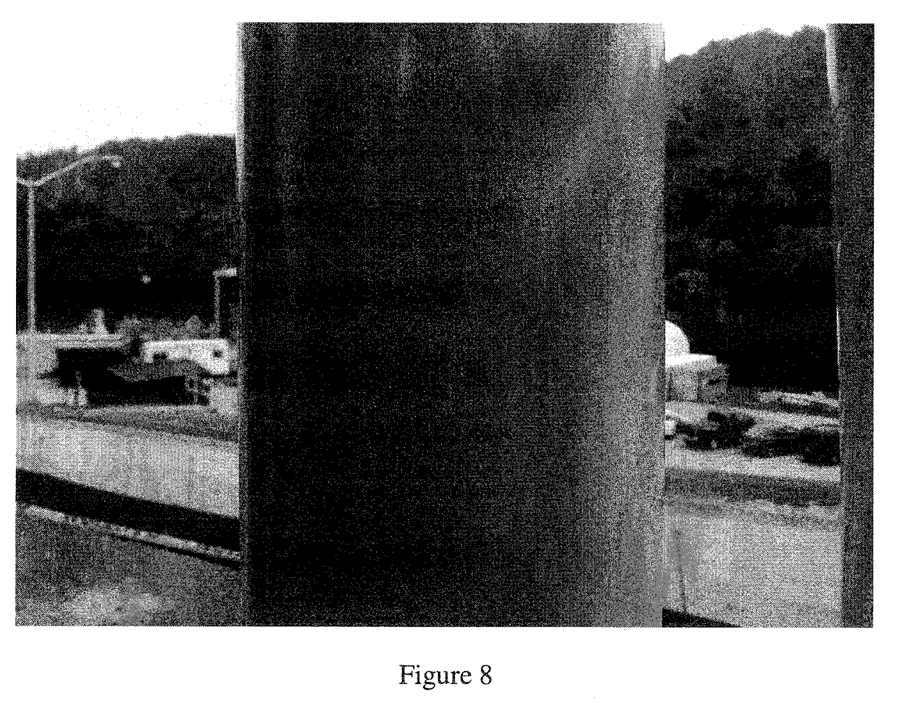
FIG. 8 is a photograph showing a fine gas-liquid dispersion produced by the experimental apparatus of FIG. 5.

This example shows the feasibility of achieving high gas transfer and good gas dispersion using a gas injector located proximate the top of a fermentation vessel that receives a low pressure gas input stream and produces a gas-liquid dispersion that travels downward for approximately 20 meters in a confined conduit for discharge into the bottom of the vessel. The same test apparatus as depicted by FIGS. 5 and 6 and described in Example 1 was used in this Example 2. The liquid in the vessel and circulating through the system in this Example comprised water amended with approximately 500 mg/L of Ethanol and 500 mg/L of Acetic Acid (Amended Water). The amended water shows the effect of having a liquid product that reduces surface tension in a fermentation liquid. Conditions during the test period included a total liquid depth of 19 meters feet in the vessel, a temperature of 25.3° C. and barometric pressure of 738 mm Hg. Using a primary liquid flow rate of 320 liters per minute and a secondary liquid flow rate of 690 liters per minute it was found that the maximum gas to liquid ratio at the outlet of the nozzle that could be achieved was 4.02 $Nm^3/m^3$. Higher gas to liquid ratios resulted in the formation of large gas bubbles. Thus in comparison to Example 1, the 4.02 gas to liquid ratio is more than 5.8 times higher. The inlet pressure of the air into the gas injector was 90 kPa. FIG. 8 shows a photo of the typical gas mixing achieved with the amended water. FIG. 8 illustrates that the gas bubble dispersion was so small that no individual bubbles are visible to the eye and the clear plastic pipe of the downcomer appears opaque. Thus this example shows that the addition of the surface tension reducing product promoted a highly dispersed gas phase in the form of microbubbles that remained in dispersion over the 20 meter length of the downcomer.

The air flow was maintained constant at a value of 1200 liters per minute until the dissolved oxygen appeared to reach steady state concentration at the different sampling stations. The dissolved oxygen concentrations versus different sampling heights are presented in Table 2. The results indicate that the gas transfer rate is more rapid than the liquid mixing rate. At all depths the measured dissolved oxygen was less then the calculation of dissolved oxygen with the greater depths having greater dissolved oxygen.

TABLE 2

| Sampling Depth (Feet from Bottom) | Measured D.O. (mg/L) | Calculated Saturated D.O. (mg/L) | Percent of Saturation |
| --- | --- | --- | --- |
| 10 | 17.9 | 21.2 | 84.4 |
| 25 | 15.3 | 17.6 | 87.3 |
| 40 | 12.4 | 13.9 | 89.1 |
| 55 | 9.6 | 10.2 | 93.9 |

What is claimed is:

1. A process for converting a feed gas stream, comprising at least one of CO or a mixture of $CO_2$ and $H_2$, to a liquid product by contact with a fermentation liquid wherein the liquid product reduces the surface tension of the fermentation liquid, said process comprising:
   a) retaining an aqueous fermentation liquid comprising a liquid product and microorganisms in a bioreactor vessel that extends vertically to height such that the fermentation liquid creates more than 100 kPa of hydrostatic pressure;
   b) withdrawing fermentation liquid containing the liquid product from said vessel at a withdrawal point and pumping a portion of said fermentation liquid as a primary working fluid to a primary gas injector;
   c) passing at least a portion of the feed gas stream into the primary gas injector at a pressure of not more than 100 kPa gauge;
   d) mixing the feed gas stream with the primary working fluid and using the pumping of the primary working fluid as the primary energy input to produce a primary gas-liquid dispersion from the feed gas stream and the primary working fluid that flows out of the gas injector and contains microbubbles;
   e) adding a supplemental working fluid to the primary gas-liquid dispersion from the primary gas injector to produce a primary mixed dispersion containing microbubbles;
   f) passing at least a portion of one of the primary mixed dispersion or the primary gas-liquid dispersion into the inlet of a primary dispersion conduit having a vertical length of at least 10 meters;
   g) discharging the primary mixed dispersion from the primary dispersion conduit into the vessel at a primary discharge point located at least 10 meters below the primary gas injector, wherein the addition of supplemental working liquid in accordance with step e) takes place at location that is downstream of the mixing of the feed gas stream with the primary working fluid and upstream of the primary discharge point;
   h) converting at least one of the CO or the mixture of $CO_2$ and $H_2$ to the liquid product in said vessel by contact of the microorganisms with the fermentation liquid that contains dissolved and un-dissolved feed gas from the primary mixed dispersion; and,
   i) passing a portion of the fermentation liquid from the vessel to a product recovery zone and recovering a product stream comprising the liquid product from said product recovery zone.

2. The process of claim 1 wherein the vertical location of the primary gas injector is above the highest fermentation liquid level in the vessel and the hydrostatic pressure at the primary discharge point is at least 150 kPa gauge.

3. The process of claim 1 wherein the cross sectional flow area of the primary dispersion conduit does not increase along the downward flow path of the primary gas-liquid dispersion.

4. The process of claim 1 wherein the liquid product comprises alcohol and the fermentation liquid contains alcohol at a total concentration of at least 0.05 wt %.

5. The process of claim 1 wherein the liquid product comprises at least one of ethanol, propanol, n-butanol, acetic acid, propionic acid and butyric acid.

6. The process of claim 1 wherein at least one of the primary gas injector and the secondary gas injector comprises a venturi-type eductor, a jet injector or a slot injector.

7. The process of claim 1 wherein:
   the feed gas stream comprises a syngas stream and a separate gas recycle stream;

the syngas stream flows to the primary gas injector that receives a first portion of the fermentation liquid to produce the primary gas-liquid dispersion stream; and the gas recycle stream flows into a secondary gas injector that receives a second portion of the fermentation liquid;

the secondary gas injector mixes fermentation liquid with the gas recycle stream to produce a secondary gas-liquid dispersion and discharges the secondary gas-liquid dispersion into the vessel at location at least to 10 meters below the outlet of the secondary feed injector.

8. The process of claim 1 wherein:

the primary injector location is at least 15 meters above the withdrawal point;

at least a portion of the feed gas stream comprises an off-gas stream from the vessel; and the feed gas stream and the off-gas stream enter the primary gas injector at a pressure greater than atmospheric pressure.

9. The process of claim 1 wherein:

the feed gas stream comprises a syngas stream and a separate off-gas stream;

the syngas stream flows at pressure greater than atmospheric into the primary gas injector that receives a first portion of the fermentation liquid to produce the primary gas-liquid dispersion stream;

the off-gas stream flows at a pressure greater than atmospheric into a secondary gas injector that receives a second portion of the fermentation liquid and mixes fermentation liquid with the gas recycle stream to produce a secondary gas-liquid dispersion; and the secondary gas injector discharges the secondary gas-liquid dispersion into the vessel at location at least 10 meters below the outlet of the secondary feed injector.

10. The process of claim 1 wherein the feed gas stream flows to the primary gas injector that receives a first portion of the fermentation liquid and at least one of a portion of an off-gas stream or a portion thereof and the feed gas stream flows to a secondary gas injector that receives a second portion of the fermentation liquid.

11. The process of claim 1 wherein the vertical location of the primary gas injector is above the surface of the liquid.

12. The method of claim 1 wherein the microorganisms comprise a mono-culture or a co-culture of any of *Clostridium ragsdalei, Butyribacterium methylotrophicum, Clostridium Ljungdahli, Clostridium Coskatii* and *Clostridium Autoethanogenum.*

13. The process of claim 1 wherein the supplemental working fluid comprises fermentation liquid.

14. The process of claim 1 wherein the supplemental working fluid is withdrawn from the vessel at the withdrawal point for the primary working fluid.

15. The process of claim 1 wherein the primary gas injector receives the supplemental working fluid and the supplemental working fluid combines with the gas-liquid dispersion in the primary gas injector to produce the primary mixed dispersion.

16. The process of claim 15 wherein the primary gas injector:

mixes the feed gas with the primary working fluid to produce the gas-liquid dispersion; passes the gas-liquid dispersion through a discharge opening located within the gas injector;

mixes, according to step d) of claim 1, the gas-liquid dispersion with the supplemental fluid downstream of the discharge opening in an integral chamber of the primary gas injector located downstream of the discharge opening to produce the primary mixed dispersion; and, discharges the mixed gas dispersion into the primary dispersion conduit.

17. The process of claim 1 wherein at least a portion of the microbubbles in the primary mixed dispersion remain dispersed over the full length of the dispersion conduit.

18. The process of claim 1 wherein the bioreactor vessel comprises a retention volume of at least 4,000 m$^3$.

19. The process of claim 1 wherein:

the primary injector location is at least 15 meters above the withdrawal point;

at least a portion of the feed gas stream comprises an off-gas stream from the vessel; and the feed gas stream and the off-gas stream enters the primary gas injector at a pressure lower than atmospheric pressure.

20. The process of claim 1 wherein the bioreactor vessel is a deep fermentation vessel.

21. The process of claim 20 wherein at least a portion of the feed gas stream comprises an off-gas stream from the bioreactor vessel and the bioreactor vessel is used to operate a bubble column or continuous stirred reactor.

* * * * *